United States Patent

Kunze et al.

[11] Patent Number: 4,506,547
[45] Date of Patent: Mar. 26, 1985

[54] APPARATUS FOR USE IN THERMOMECHANICAL ANALYSIS

[75] Inventors: Wolfgang Kunze, Rodgau; Bernd Schweckendieck, Gr. Umstadt, both of Fed. Rep. of Germany

[73] Assignee: Bodenseewerk Perkin-Elmer & Co., GmbH, Uberlingen, Fed. Rep. of Germany

[21] Appl. No.: 481,545

[22] Filed: Apr. 4, 1983

Related U.S. Application Data

[63] Continuation of Ser. No. 420,977, Sep. 21, 1982, abandoned.

[30] Foreign Application Priority Data

Sep. 22, 1981 [DE] Fed. Rep. of Germany ....... 3137603

[51] Int. Cl.³ ............................................ G01N 11/12
[52] U.S. Cl. ...................................... 73/150 R; 73/85
[58] Field of Search .................. 73/150 A, 150 R, 85; 33/DIG. 1, DIG. 5

[56] References Cited

U.S. PATENT DOCUMENTS

| 989,471 | 4/1911 | Abraham | 73/150 |
| 2,427,866 | 9/1947 | MacGeorge | 33/DIG. 5 |
| 2,801,537 | 8/1957 | Kabelitz | 73/150 |
| 3,150,523 | 9/1964 | Papsis | 73/150 |

FOREIGN PATENT DOCUMENTS 170879 5/1905 Fed. Rep. of Germany ........ 73/451

Primary Examiner—Steven L. Stephan
Assistant Examiner—Denis E. Corr
Attorney, Agent, or Firm—F. L. Masselle; E. T. Grimes; J. D. Crane

[57] ABSTRACT

Apparatus for use in conducting both static and dynamic thermomechanical analysis includes a load member, one end of which is supported by the sample located in a sample receptacle, eventually in a selected gas atmosphere, in heat equilibrium and the other end of which is loaded statically by a weight or dynamically by the armature of an electromagnet.

3 Claims, 2 Drawing Figures

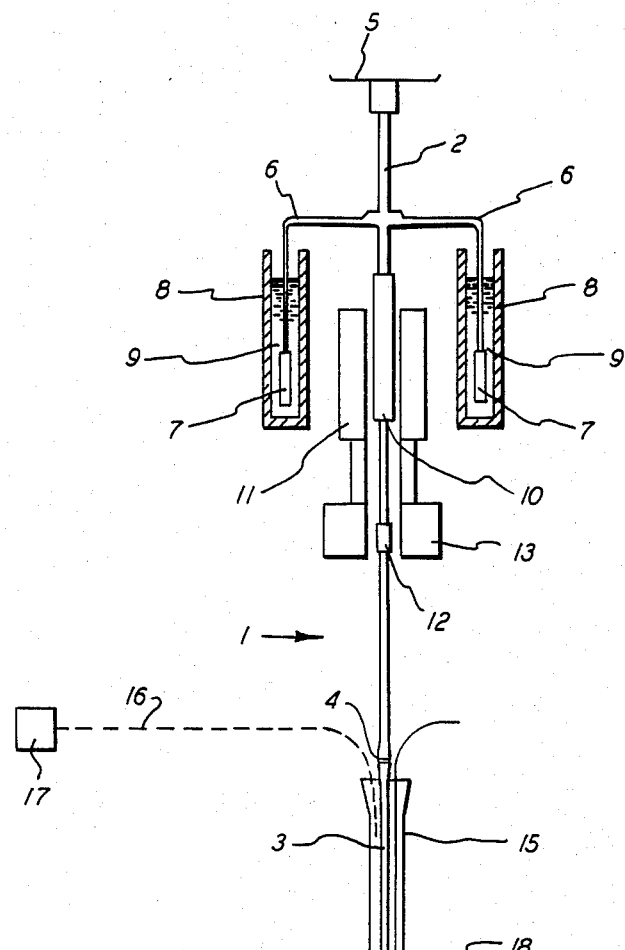
FIG.1
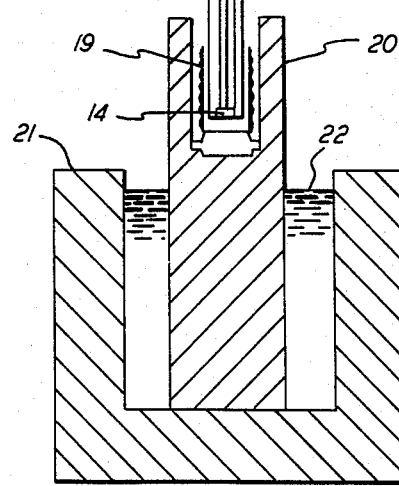

APPARATUS FOR USE IN THERMOMECHANICAL ANALYSIS

This is a continuation of U.S. patent application Ser. No. 420,977, filed Sept. 21, 1982, now abandoned.

BACKGROUND OF THE INVENTION

The present invention generally relates to an apparatus for use in thermomechanical analysis and, in particular, relates to an apparatus adapted to perform both static and dynamic thermomechanical measurements without changing the loading means.

Apparatus of this kind is employed to investigate the mechanical behavior of, inter alia, plastics or plastic film coatings as a function of load and temperature. Conventionally, measurements are performed over a temperature range extending from a temperature far below the glass transition temperature to a temperature near the distortion temperature. Static loading techniques are generally employed, depending on the size of the load, for measuring the expansion of the sample or the depth of penetration of the probe into the sample. Dynamic loading techniques are usually used to determine the elastic, the plastic or the permanent deformation of the sample. Knowledge of such properties is important for the investigation of the mechanical properties of most materials, for example lacquers.

One conventional apparatus is described by K. H. W. Reichert and G. Donnebrink as published under the title "Eine modifizierte Form der thermomechanischen Analysen zur Messung der temperaturabhangigen Eigenschaften von Anstrichfilmen" in the Journal "farbe+lack", vol. 86, issue no. 7, page 591, in 1980. In the apparatus described therein, the load member forms a piston-like probe one end of which is supported by the sample in a sample tube and the other end of which carries a weight tray, the sample becoming statically loaded by weights put onto the latter. The sample tube is provided with a gas introduction means and with cooling means while the sample is provided with a thermocouple. The piston-like probe is guided by guiding means and includes a magnet member forming a solenoid plunger which coacts with an axially displaceable measuring coil forming the position signalling means. The measuring coil encircles the solenoid plunger to form a displacement transducer the output signals of which indicate the displacement of the solenoid plunger from a zero position. These signals are recorded by any recorder means. A compensation spring is used to compensate the piston-like probe for its own weight. In the same apparatus the sample may also be loaded dynamically. However, to accomplish the dynamic loading, the armature of an electromagnet is placed on the weight tray. The armature is adapted to periodically oscillate by an electromagnet which is excited according to selectable periodic functions of time. Thus, the oscillations effectively provide alternating load and relief pulses to the sample. The oscillator characteristic of the piston-like probe is affected by the mechanical properties of the sample and by the temperature and are also recorded by the recorder.

In adapting the apparatus from measuring static loads to dynamic loads, a change in the loading means is required. The measuring coil must be readjusted after each exchange of the loading means because of the changes in the weight of the load member. Further, care must be exercised for the armature and the electromagnet to assume the same relative initial position as far as possible since otherwise the loads eventually may not be comparable. In addition, to avoid erroneous results operation must remain within the effective range of the compensating spring and that this range can not be exceeded during the application of the load to the sample.

SUMMARY OF THE INVENTION

Accordingly, one object of the present invention is to provide an apparatus which may be utilized for static as well as for dynamic thermomechanical measurements without requiring a change in the loading means.

This object is achieved, at least in part, by an apparatus having the load member floatingly mounted and the armature of the electromagnet undisplaceably connected thereto.

In one embodiment according to the invention both the magnet member of the position signalling means and the armature of the electromagnet are undisplaceably mounted to the load member. Thus, no major adjustments are necessary on changing from static to dynamic loads, and further adjustment is simultaneously performed for both kinds of measurement. The floating suspension of the load member is of particular significance in this respect since with this kind of support the load member is always compensated for its own weight.

Further, the fixed position of the electromagnet relative to the position signalling means is of advantage insofar as thereby simultaneous adjustment of the position signalling means and of the electromagnet is permitted which considerably simplifies and facilitates the adjustment because adjustment of one of said members will be sufficient. Conveniently therefor, an elongate housing is provided for the position signalling means, said housing being closed at both its ends and the ends being provided with passages for the load member, and a carrier member for the electromagnet is mounted to the end of the housing which is remote from the sample.

It is specifically advantageous that the armature is made of a premagnetized magnetic material. Thereby, under dynamic loads, a linear relation always exists independent of hysteresis between current flow through the electromagnet and the force generated which acts on the load member and on the sample, respectively.

Other objects and advantages will become apparent to those skilled in the art from the following detailed description and drawing affixed hereto.

BRIEF DESCRIPTION OF THE DRAWING

The drawing, not drawn to scale, includes:

FIG. 1, which is a schematic illustration of an apparatus embodying the principles of the present invention.

DETAILED DESCRIPTION OF THE INVENTION

Figure 2:
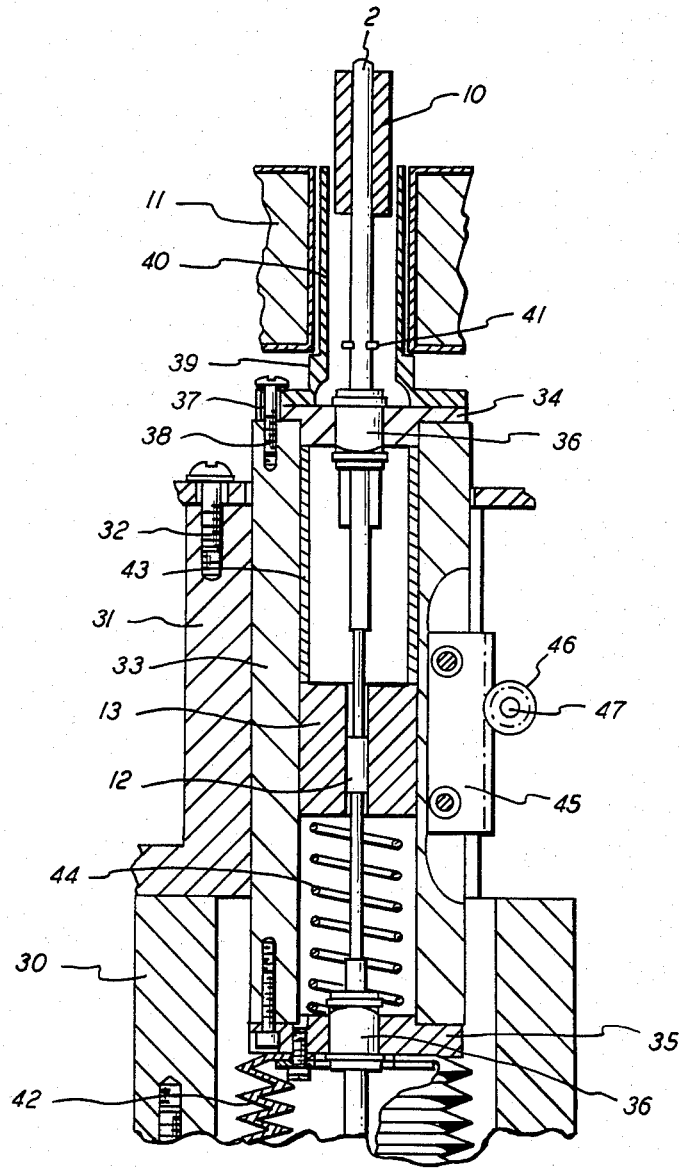
FIG. 2, which is a sectional view of the members acting on the load member in a measurement using the apparatus shown in FIG. 1.

With reference to a preferred embodiment, the schematic illustration of which is shown in FIG. 1, a load member 1 comprises an upper portion 2 and a lower portion 3 which are releasably interconnected by, for example, a threaded coupling 4. At its free end upper portion 2 carries a plate 5 used to receive a loading weight to apply a static load. Three angled arms 6 extend from the upper portion 2 to both sides of load member 1, the free ends thereof carry immersion members 7, each being immersed in an immersion means. The immersion means preferably comprising a chamber 8 and an oil filling 9. An armature 10 is mounted at the upper part 2 below angled arms 6 and coacts with an electromagnet 11. The armature 10 is made of premagnetized magnetic material; such magnetic materials are known and consist of, for example, plastic-imbedded parts of an alloy comprising substantially rare earths and cobalt (-Magnet; IBS Magnet-Service, Berlin). The prefabricated armature 10 is provided with an internal bore cooperatively adapted to the outer diameter of the upper part 2 and is rigidly affixed, or mounted, thereto after premagnetization by, for example, glueing. The electromagnet 11 can be of conventional design and may be excited by, for example, an alternating current of a character which is selected in adaptation to the desired investigation purpose. Below the armature 10 a magnet member 12 is undisplaceably mounted to the upper part 2 and positioned within the interior of position signalling means 13. The position signalling means 13 can be constituted by an LVDT (linear variable differential transformer) usually employed in apparatus of this kind and responds to positional changes of the magnet member 12 by generating a measuring signal recorded by recording means (not shown). As indicated in FIG. 1, the electromagnet 11 and the position signalling means 13 are interconnected.

While the upper part 2 of the load member 1 is designed to coact with the means required for carrying out the measurement, the lower part 3 is designed for interaction with the sample 14. The sample 14 to be investigated is located at the bottom of a sample receptacle 15 which is open at the top. The open end of the sample receptacle 15 is connected to the feed line 16 of gas introducing means 17 for displacing the air from the sample receptacle 15 and replacing the same with any other respectively desired gas. The free end of lower part 3 of the load member 1 is supported at the sample 14. Additionally, a thermocouple 18 is inserted into the sample receptacle 15 and placed close to the sample 14. The sample receptacle 15 is provided at its closed end in the range of the sample 14 with a heater coil 19 connected to a current source (not shown); the closed end of the sample receptacle 15 is positioned within a recess in an aluminum block 20 forming a heat sink which is disposed within an insulating container 21 holding a coolant 22, such as solid carbon dioxide or liquid nitrogen.

FIG. 2 illustrates the structure of the measuring means in detail. For clarity, features which correspond to those shown in FIG. 1 are designated with the same reference numerals. In FIG. 2, that portion of the apparatus is illustrated which extends in the region from the angled arms 6 to the threaded coupling 4. In the upper portion of FIG. 2, the armature 10 at the upper part 2 of load member 1 is shown and in the lower portion thereof part of a casing 30 housing the apparatus is also shown. Guiding means 31 are secured to the casing 30 and carry the chamber 8 receiving the immersion member, not shown in the drawing, by means of screws 32. The guiding means 31 guides therein an elongated cylindrical housing 33, which housing 33 is closed at both ends with closing plates 34, 35 having passages 36 therethrough for the upper part 2. A carrier member 37 is secured to the upper closing plate 34 by means of screws 38, the carrier member 37 forming an annular plate having a central aperture adapted to the passage 36 and a socket 39 from which a tube 40 projects upwardly. The outer diameter of the tube 40 is adapted to the internal diameter of the central gap in the electromagnet 11 which is supported at the front end of the socket 39. In this region, the upper part 2 has a stop ring 41 limiting the downwardly directed movement of the load member 1. Lower closing plate 35 is connected to the casing 30 by means of a bellows 42 protecting the interior of housing 33 from dirt.

The position signalling means 13 is located within housing 33 and encircles the magnet member 12 fixed to the upper part 2; the supply leads therefor are passed through the housing 33 and through the guiding means 31 to the connector plate (not shown) at the casing 30. With its upper end face the position signalling means 13 abuts a stop 43 placed at the interior wall of the housing 33 which stop 43, in this embodiment, forms a bushing snugly fitted into the housing 33 and abutting the interior face of the upper closing plate 34. With its lower end face the position signalling means 13 is supported by a supporting spring 44 reacted at the interior face of the lower closing plate 35.

The housing 33 is provided with a rack member 45 extending at the outer face thereof in a range exceeding the axial length of the position signalling means 13 and in parallel with respect to the axis of the housing 33, the teeth of the rack member 45 being directed outwardly. A pinion 46 meshes with the rack member 45 and is arranged at a rotatable shaft 47 extending normally with respect to the plane of the drawing and of the axis of the housing 33, respectively. The guiding means 31 include a longitudinal slot aligned with the rack member 45 and the casing 30 includes a passage for the rotatable shaft 47.

The apparatus as described hereinbefore operates as follows:

The load member 1, which is relieved of its own weight by the floating mount in chamber 8 is placed on the sample 14 inserted into sample receptacle 15, after temperature equilibration is achieved and after, if desired, a required gas atmosphere is provided in the sample receptacle 15 via gas introducing means 17. Prior to the actual measurement an adjustment with respect to the position signalling means 13 is performed by adjusting the housing 33 by means of the rotatable shaft 47 and the pinion 46 engaging rack member 45, this being permitted by the longitudinal slot in guiding means 31 and by the passage of the rotatable shaft 47 through the casing 30. Thereby the housing 33 is displaced relative to the load member 1 in the guiding means 31 until the indication at the recording means shows the magnet member 12 to be in the zero position. Simultaneously therewith, the electromagnet 11 is displaced so that it is ensured that in each measurement both the electromagnet 11 and the armature 10 have the same relative initial position. The measurement, then, is performed in the known manner using static or dynamic loads without intermediate readjustment if the conditions of load are changed which even may be changed while investigating one and the same sample 14.

Although the present invention has been described herein with reference to a particular exemplary embodiment other mechanism and configurations can also be made without departing from the scope and spirit of the present invention. Hence, this description is not deemed to be limiting and the present invention is considered to be limited only by the claims and the reasonable interpretation thereof.

What is claimed is:

1. Apparatus for thermomechanical analysis of a sample, said apparatus comprising, in combination:
    a load member, said load member being guided in the vertical direction;
    a sample receptacle in which one end of said load member is supported by said sample, said receptacle being provided with means for introducing a gas thereinto during said analysis;
    means for controllably varying the temperature of said sample receptacle over a preselected range;
    a magnetic member undisplaceably connected to said load member;
    an electromagnetic position signalling means interacting with said magnetic member, said position signalling means being adapted for adjustment into a zero position by adjusting means and having an output which provides a measuring signal corresponding to the displacement of said magnetic member from said zero position;
    a plate, proximate the other end of said load member and connected thereto, for receiving a weight whereby said sample is subjected to a static load;
    means, affixed to said load member between said plate and magnetic member, for floatingly mounting said load member; said means including at least one immersion member and a container for an immersion medium in which said immersion member is received;
    means for subjecting said sample to a dynamic load, said dynamic loading means including an electromagnet and an armature, said armature being connected to said load member;
    means for recording said measuring signals as a function of temperature;
    said load member being provided intermediate said plate and said signaling means with three angled arms at the free ends of which said immersion members are disposed; and
    said container forms a chamber comprising an oil filling and a separate chamber is provided for each said immersion chamber.

2. Apparatus for thermomechanical analysis of a sample comprising, in combination;
    a load member, said load member being guided in the vertical direction;
    a sample receptacle in which one end of said load member is supported by said sample, said receptacle being provided with means for introducing a gas thereinto during said analysis;
    means for controllably varying the temperature of said sample receptacle over a preselected range;
    a magnetic member undisplaceably connected to said load member;
    an electromagnetic position signaling means interacting with said magnetic member, said position signaling means being adapted for adjustment into a zero position by adjusting means and having an output which provides a measuring signal corresponding to the displacement of said magnetic member from said zero position;
    a plate, proximate the other end of said load member and connected thereto, for receiving a weight whereby said sample is subjected to a static load;
    means, affixed to said load member between said plate and said magnetic member, for floatingly mounting said load member; said means including at least one immersion member and a container for an immersion medium in which said immersion member is received;
    means for subjecting such sample to a dynamic load, said dynamic loading means including an electromagnet and an armature, said armature being connected to said load member;
    means for recording said measuring signals as a function of temperature;
    said armature being mounted to said load member intermediate said magnetic member and said angle arms and said electromagnet is fixidly mounted with respect to said position signaling means but adjustably thereto;
    an elongated housing is provided for said position signalling means, said housing being closed at both ends, said ends being provided with passages for said load member;
    a carrier member for said electromagnet being mounted to the end of said housing which is remote from the sample, said housing being guided for vertical movement relative to said position signaling means by a guiding member, said housing being provided on an exterior face thereof with a vertically extending rack member protruding from said guiding member through a longitudinal slot therein, said rack member being engaged with a pinion mounted to a rotatable shaft extending normally with respect to said housing.

3. Apparatus as claimed in claim 2 wherein said housing is slidably movable with respect to said position signalling means and said position signalling means is held in abutment to a stop formed within said housing under said load of a supporting spring which is supported at the end of said housing which faces the sample.

* * * * *